United States Patent
Green et al.

(10) Patent No.: US 7,274,450 B1
(45) Date of Patent: *Sep. 25, 2007

(54) SAMPLE ENTRY PURGE SYSTEM IN SPECTROPHOTOMETER, ELLIPSOMETER, POLARIMETER AND THE LIKE SYSTEMS

(75) Inventors: Steven E. Green, Lincoln, NE (US); Ping He, Lincoln, NE (US); Galen L. Pfeiffer, Lincoln, NE (US); Brian D. Guenther, Lincoln, NE (US); Gerald T. Cooney, Lincoln, NE (US); John A. Woollam, Lincoln, NE (US); Martin M. Liphardt, Lincoln, NE (US); Blaine D. Johs, Lincoln, NE (US); Craig M. Herzinger, Lincoln, NE (US)

(73) Assignee: J.A. Woollam Co., Inc, Lincoln, NE (US)

( * ) Notice: Subject to any disclaimer, the term of this patent is extended or adjusted under 35 U.S.C. 154(b) by 507 days.

This patent is subject to a terminal disclaimer.

(21) Appl. No.: 10/857,774

(22) Filed: May 28, 2004

Related U.S. Application Data

(63) Continuation-in-part of application No. 10/376,677, filed on Feb. 28, 2003, now Pat. No. 6,982,792, and a continuation-in-part of application No. 09/531,877, filed on Mar. 21, 2000, now Pat. No. 6,535,286.

(60) Provisional application No. 60/480,851, filed on Jun. 24, 2003, provisional application No. 60/424,589, filed on Nov. 7, 2002, provisional application No. 60/427,043, filed on Nov. 18, 2002, provisional application No. 60/431,489, filed on Dec. 6, 2002.

(51) Int. Cl.
*G01J 4/00* (2006.01)

(52) U.S. Cl. ..................... 356/369; 356/244

(58) Field of Classification Search ............... 356/369, 356/244
See application file for complete search history.

(56) References Cited

U.S. PATENT DOCUMENTS

| | | | |
|---|---|---|---|
| 4,210,401 A | 7/1980 | Batten | 356/369 |
| 4,472,633 A | 9/1984 | Motooka | 250/338 |
| 4,596,462 A * | 6/1986 | Helphrey | 356/300 |
| 4,640,617 A * | 2/1987 | Hughes et al. | 356/326 |
| 4,657,390 A * | 4/1987 | Doyle | 356/451 |
| 5,045,701 A | 9/1991 | Goldstein et al. | 250/339 |
| 5,045,704 A | 9/1991 | Coates | 250/372 |
| 5,177,561 A * | 1/1993 | Milosevic et al. | 356/326 |
| 5,486,701 A | 1/1996 | Norton et al. | 250/372 |
| 5,582,646 A | 12/1996 | Woollam et al. | 118/708 |
| 5,661,589 A | 8/1997 | Meyer | 359/232 |
| 5,706,212 A | 1/1998 | Thompson et al. | 364/525 |
| 5,757,494 A | 5/1998 | Green et al. | 356/369 |
| 5,872,630 A | 2/1999 | Johs et al. | 356/369 |
| 5,956,145 A | 9/1999 | Green et al. | 356/364 |

(Continued)

*Primary Examiner*—Roy M. Punnoose
(74) *Attorney, Agent, or Firm*—James D. Welch

(57) ABSTRACT

A sample sequestering system which allows access to a subspace in a chamber encompassed generally enclosed space, for use in entering and removing a sample when the subspace is opened to atmosphere. Sufficient purge gas is flowed from within the generally enclosed space into the subspace discourage atmospheric contaminates from entering into the subspace. Contained within the generally enclosed space is a spectrophotometer, ellipsometer or polarimeter or the like system which operates at wavelengths, (eg. UV), which are adversely affected, (eg. absorbed), by typical atmospheric contents.

9 Claims, 11 Drawing Sheets

U.S. PATENT DOCUMENTS

| | | | |
|---|---|---|---|
| 5,963,327 A | 10/1999 | He et al. | 356/369 |
| 6,034,777 A | 3/2000 | Johs et al. | 356/369 |
| 6,414,302 B1 | 7/2002 | Freeouf | 250/225 |
| 6,456,376 B1 | 9/2002 | Liphardt et al. | 356/369 |
| 6,535,286 B1 | 3/2003 | Green et al. | 356/369 |
| 6,813,026 B2 * | 11/2004 | McAninch | 356/445 |
| 2002/0024668 A1 | 2/2002 | Stehle et al. | |

* cited by examiner

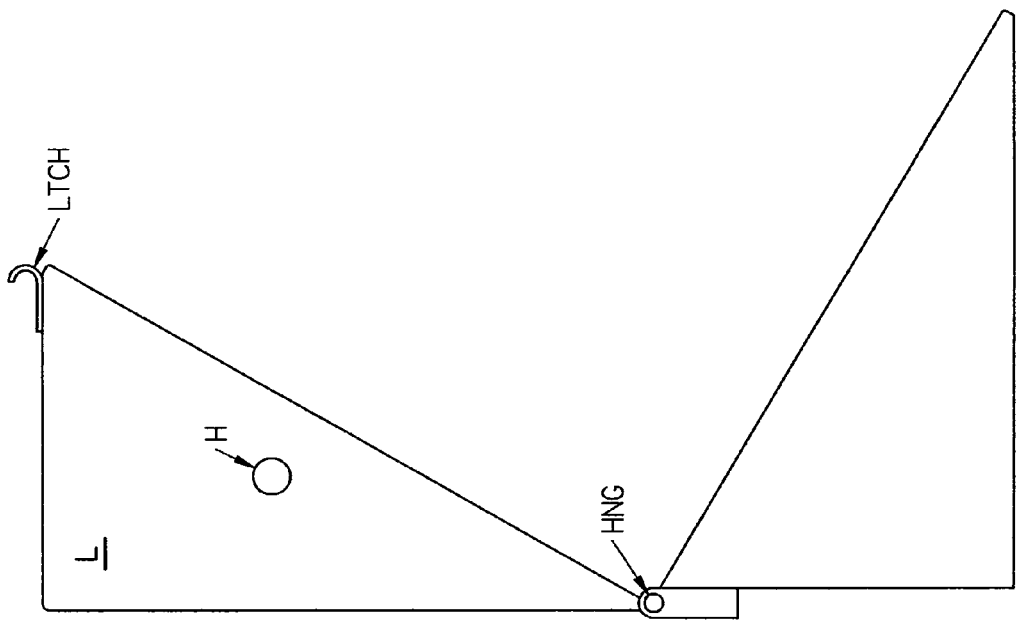
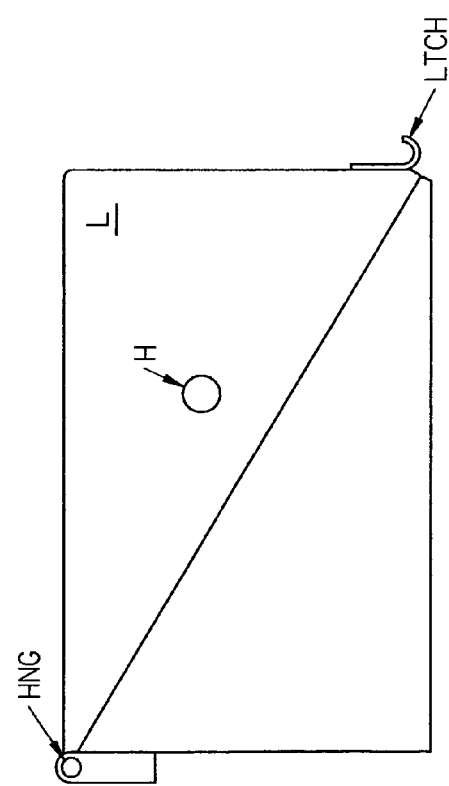
FIG. 5b
FIG. 5a

SAMPLE ENTRY PURGE SYSTEM IN SPECTROPHOTOMETER, ELLIPSOMETER, POLARIMETER AND THE LIKE SYSTEMS

This application is a Continuation-In-Part of Utility application Ser. No. 10/376,677 Filed Feb. 28, 2003 now U.S. Pat. No. 6,982,792 and therevia of Ser. No. 09/531,877 Filed Mar. 21, 2000, (now U.S. Pat. No. 6,535,286); and from is a Continuation-In-Part of Co-Pending Utility application Ser. No. 10/376,677 Filed Feb. 8, 2003; and Claims benefit of Provisional Application Ser. Nos. 60/480,851 Filed Jun. 24, 2003, 60/424,589 filed Nov. 7, 2002, 60/427,043 filed Nov. 18, 2002 and 60/431,489 filed Dec. 6, 2002.

TECHNICAL FIELD

The disclosed invention relates to methods of entering samples into spectrophotometer, ellipsometer or polarimeter or the like system systems, and more particularly to a sample sequestering system which allows access to a subspace in a chamber encompassed generally enclosed space. The sample sequestering system allows entering and removing a sample when the subspace is opened to atmosphere. Sufficient purge gas can be flowed from within the generally enclosed space into the subspace to discourage atmospheric contaminates from entering thereinto.

BACKGROUND

Spectroscopic Ellipsometry (SE) was developed in the early 1970's after single wavelength ellispometry had gained widespread acceptance. The first (SE) systems provided limited Ultraviolet (UV) to near Infrared (IR) spectral range capability, and with the exception of a few research instruments, this remained the case until the 1990's. Many challenges faced development of (VUV) ellipsometer systems, including the fact that many optical element materials absorb in the (VUV) wavelength range. Vacuum Ultraviolet (VUV) ellipsometry was so named as it was initially carried out in vacuum, however, the terminology is today applied where purging gas such as nitrogen is utilized in place of vacuum at wavelengths, typically with an energy less than about 10 ev. The reason (VUV) ellipsometry must be carried out in vacuum or purging gas is that (VUV) wavelengths, are absorbed by oxygen and water vapor.

In the mid-1980's a Spectroscopic ellipsometer was constructed at the BESSY Synchrotron in Berlin for application in the (VUV) wavelength range, (eg. 5-35 eV), and in the 1990's Spectroscopic ellipsometry was achieved in the Extreme Ultraviolet (EUV) range, (eg. greater than 35 eV), at KEK-PF. Application of ellipsometry in the (VUV) and (EUV) wavelength ranges remained restricted to said research facilities until in 1999 commercial (VUV) ellipsometer systems became available from companies such as the J.A. Woollam Co. Inc. At present there are approximately twenty-five (VUV) Systems in use worldwide. It is noted that commercial (VUV) instruments, which provided wavelengths down to 146 nm, were introduced in response to the need for bulk material properties at 156 nm, which is utilized in lithography as applied to semiconductor gate oxide production.

A known patent which provides for use of VUV wavelength electromagnetic radiation through 10 eV is U.S. Pat. No. 6,414,302 B1 to Freeouf.

The practice of ellipsometry, polarimetry, spectrophotometry, reflectometry, scatterometry and the like, using Infrared (IR), (eg. 2-33 micron), and Ultraviolet (UV), (eq. 135-1700 nm), Electromagnetic Radiation Wavelengths, then is, as disclosed above, known. As mentioned, electromagnetic Radiation with wavelengths below about 190 nm is absorbed by atmospheric components such as oxygen and Water Vapor. Thus, practice of Ellipsometry etc. using UV Wavelengths is typically carried out in vacuum or an atmosphere which does not contain oxygen and/or water vapor or other absorbing components. The J.A. Woollam CO. VUV-VASE, (Registered Trademark), for instance, utilizes a substantially enclosed Chamber which encompasses a substantially enclosed space which during use is purged by Nitrogen and/or Argon or functionally equivalent gas. (Note Nitrogen does not significantly absorb UV Range wavelengths, and Argon is in some respects even a better choice). Further, the source of the electromagnetic radiation in the J.A. Woollam CO. VUV-VASE is preferably a Deuterium Lamp and/or a Xenon Lamp, which produce wavelengths of 115-400 nm, (of which 135-190 nm is used), and up to about 2000 nm, respectively. Specific wavelengths are selected by a J.A. Woollam Co. Monochromator which is a Cherny-Turner type Spectrometer sequentially comprising, mounted inside an enclosing means;

a) source means for providing of a beam including ultraviolet wavelength range electromagnetic radiation;
b) a first slit;
c) a first spherical mirror;
d) a first stage comprising a plurality of gratings, each of which can be rotated into a functional position;
e) a second spherical mirror;
f) a second slit;
g) a third spherical mirror
h) a second stage comprising a plurality of gratings, each of which can be rotated into a functional position;
i) a forth spherical mirror; and
j) a pin hole;

and further comprising a beam chopping means present between said source means and said pin hole;

such that in use an electromagnetic beam from said source of the electromagnetic radiation is:
 caused pass through said first slit;
 reflect from said first spherical mirror;
 interact with one of said plurality of gratings on said first stage which is rotated into a functional position;
 reflect from said second spherical mirror;
 pass through said second slit;
 reflect from said third spherical mirror;
 interact with one of said plurality of gratings on said second stage which is rotated into a functional position;
 reflect from said forth spherical mirror; and
 exit through said pinhole;

and at some point in said progression be subjected to chopping.

The gratings on said first and second stages are separately rotated into precise desired functional positions via stepper motors controlled by computer. This has proven to provide superior precision, repeatability and speed of achieving the desired wavelength than commercially available grating positioning systems in which both gratings are simultaneously controlled. Further, an electromagnetic radiation beam produced by said Monochromator has been shown to provide a highly collimated beam, with typical defining parameters being a 5 mm diameter at the pinhole output of the Monochromator, with divergence to about 20 mm diameter at 20 Feet, (ie. 6000 mm). This represents a divergence angle of only about 0.00125 radians, (ie. 0.07 Degrees).

It is further disclosed that the chopper means comprises a lock-in amplifier which chops the electromagnetic beam at a frequency which is synchronized to a detector which receives the electromagnetic beam after it interacts with a sample, (see further below). The synchronization is typically without delay, but there can be a phase relationship introduced between the beam chopping and the detection of the signal by the detector. Said lock-in amplifier is utilized to provide a better signal to noise ratio. The use of a chopping lock-in amplifier is beneficial in that background noise is eliminated. For instance, if said approach is not used it can be necessary to obtain data in a darkened room and to avoid the influence of extraneous electromagnetic radiation, or if data is obtained in a lighted room an additional background data set must be obtained using a shutter to block the beam, and then a subtraction procedure applied to compensate the data set for the background extraneous electromagnetic influence. Where chopping is utilized data can be obtained in a lighted room without the need to obtain an additional data set and apply the subtraction procedure.

Application problems have been identified with the design of the monochromator system as described, in that wiring and electronic components have to date been included inside the substantially enclosed space within the enclosure. Outgassing from wiring and electronic components etc., (as required where Vacuum-Ultraviolet (VUV) wavelengths are utilized), can require very long periods of time. Further, electrical connections to components such as the means for providing the first and second slits and rotating effecting means for the first and second stage which comprises thereupon a plurality of gratings, to date, have been hard wired thereto, thereby making replacement tedious. As insight, at this point it is noted that improvements disclosed herewithin include the use of a wire eliminating "Mother Board", inside the substantially enclosed space within the monochromator system, to which Mother Board components electrical connections are via easily removable plug-socket means. Further, electronic components are mounted to a Second Printed-Circuit Board which is mounted outside said enclosure via plug-in means, thereby making its replacement easy to accomplish without requiring opening the substantially enclosed space within the enclosure to atmosphere.

A problem with practicing Ellipsometry etc. where the sample system is in a substantially enclosed, internal ambient controlled, chamber is that it is very inconvenient to access what is contained therewithin without entering oxygen or water vapor etc. thereinto. As a result, the J.A. Woollam Co. VUV-VASE, (Registered Trademark), System comprises a means for causing a subspace sequestering means to become configured so as to sequester a sample system in a subspace of said substantially enclosed space during entry and removal of a sample system. This allows accessing a sample system means for placing and maintaining a sample system in a desired position and orientation, (ie. a sample supporting stage), with the benefit that only the sequestered subspace then needs substantial purging. The subspace sequestering means further enables reconfiguration to open the entire substantially enclosed space in the chamber to the sample system, thereby facilitating its access thereof via UV range wavelength electromagnetic radiation.

It is noted that the J.A. Woollam Co. VUV-VASE has proven to provide good data in cases even when operated without Nitrogen purging, and has been applied to obtain reflection data using an electromagnetic beam caused to approach a sample system at a normal or oblique angle of incidence, transmission data with an electromagnetic beam being caused to approach a sample system at a normal or oblique angle of incidence, using unpolarized electromagnetic radiation, or partially polarized electromagnetic radiation or polarized electromagnetic radiation. That is, very good data has been obtained utilizing unpolarized; partially polarized, randomly polarized; linearly polarized; with respect to a sample system linearly "p" polarized; with respect to a sample system linearly "s" polarized; and circularly polarized electromagnetic radiation in purged and atmospheric ambients.

The J.A. Woollam Co. VUV-VASE includes two-speed purge control means, such that a sequestered subspace can be purged, quickly, but when purging is substantially complete, a Nitrogen conserving slower maintenance purge speed can be effected.

It is further disclosed that versions of the J.A. Woollam CO. VUV-VASE which have been sold to date have included a Quad Detector having a centrally located hole therein which is 1.27 mm in diameter, which Quad Detector is mounted via a stepper motor means for moving the centrally located hole into and out of the locus of a beam of electromagnetic radiation. The Quad Detector has Four Detector Elements surrounding the centrally located hole. In use a sample system is oriented by a means for placing and maintaining a sample system in a desired position and orientation, (typically comprising a vacuum chuck to secure the sample), such that a beam of electromagnetic radiation which passes through the centrally located hole in the Quad Detector reflects directly 180 degrees back, thereby minimizing the amount of energy entering the Detector Elements. Once the sample system is so oriented, the sample system is caused to be rotated so that a perpendicular to its surface is redirected by a known number of degrees. This procedure allows setting a precise Angle-Of-Incidence of the electromagnetic beam to the sample system surface without the requirement of calibration. However, the small diameter of the centrally located hole in the Quad Detector can not be left in place during data acquisition as it reduces the intensity of the beam an unacceptable amount. Thus, versions of the J.A. Woollam CO. VUV-VASE available to date have included the mentioned motorized means inside the substantially closed Chamber to move the Quad Detector completely away from the locus of the electromagnetic beam after alignment is complete. This has led to problems such as Quad Detector socket pins eventually not lining-up properly with socket holes etc. While mounting and removing a Quad Detector is easy to practice in open air it is not convenient in a substantially enclosed space which requires purging every time it is opened to, for instance, straighten electrical pins on a Quad Detector. It is noted at this point that the disclosed invention newly provides a previously undisclosed specially designed permanently mounted Quad Detector with a larger, (eg. 2-4 mm diameter), centrally located, hole therewithin through which a beam of electromagnetic radiation can be passed during data acquisition. It has been found that about ten (10) times more electromagnetic radiation intensity passes through said larger 2-4 mm diameter hole than does through said 1.27 mm diameter hole. Further, excellent angle of incidence alignment by the procedure described above is still achievable using the new quad detector.

It is noted at this point that a patent to Johs et al. U.S. Pat. No. 5,872,630, from which this Application Continues-In-Part via other Co-Pending Applications, in Col. 20, Lines 55-57, establishes conception of the idea of applying a Quad Detector in an Automated Beam Alignment Procedure in the context of an Ellipsometer System. A fixed Quad Detector applied in an Automated Alignment Procedure which incorporates use of stepper motors to, in response to Quad Detector System Detector Elements, automatically align a Sample System, has not been previously available. This is particularly true in two cases:

- where a fixed location Quad Detector with a relatively large, (eg. 2-4 mm diameter as compared to a standard 1.27 mm hole diameter), centrally located hole therein, through which an electromagnetic beam passes during both Alignment and Data Acquisition, and
- where a Quad Detector is placed so that the electromagnetic beam does not pass therethrough during Alignment or Data Acquisition, but rather is placed such that a beam which approaches a Sample System at an oblique angle enters thereinto, typically via a beam splitter.

(Note that Quad Detectors are used as an example, and that detectors with any functional number of elements can be applied).

It is noted that while the later scenario is of benefit in that absolutely no attenuation of an electromagnetic beam is caused during Data Acquisition by the Quad Detector, it becomes necessary to then Calibrate the relationship between said oblique angle, and the orientation of the Sample System, to then enable orienting the Sample system so an electromagnetic beam approaches along a known angle of incidence thereto during Data Acquisition. Where an electromagnetic beam passes through a centrally located hole in a Quad Detector, once the Sample System is aligned so that it reflects a beam directly back 180 degrees from a surface of a Sample System, it is a relatively simple matter to then re-orient the Sample System with respect to said aligned Sample System orientation to effect a desired Angle-Of-Incidence of the electromagnetic beam to said Sample System. Hence, while placing a Quad Detector so that an electromagnetic beam does not have to pass through a centrally located hole therein enables avoiding attenuating beam intensity, said placement initiates the need to then perform a calibration procedure. It is also noted that a Quad Detector through which an electromagnetic beam need not pass, need not have a centrally located hole therein or can have a standard 1.27 mm in diameter hole therethrough, and hence can enable tighter positioning of Detector elements therein, thereby enabling slightly greater precision in Alignment than can be the case where a greatly larger diameter hole is present.

The J.A. Woollam CO. VUV-VASE is further fitted with a multiple detector system as described in Co-Owned and patent application Ser. No. 09/531,877, (now U.S. Pat. No. 6,535,286) which comprises a plurality of Detectors. The purpose is to allow easily rotating one of a plurality of Detectors into position to receive a beam of electromagnetic radiation after interaction with a sample system. Preferably each Detector has associated therewith an Analyzer, but it is possible to provide a single separately mounted Analyzer with only the plurality of Detectors. The ability to move Detectors in and out of a beam, enables easy sequential positioning of Detectors which are sensitive in different wavelength ranges. It is also noted that the ability to easily move a Detector facilitates use in "Scaterometry", wherein an electromagnetic beam is caused to interact with a sample system in a substantially fixed manner, while the Detector system is moved through a plurality of positions, at each of which positions data is obtained thereby. Electromagnetic radiation scattered to each said location is thus separately monitorable by a movable detector.

The J.A. Woollam CO. VUV-VASE System has utilized Detector Elements of Stacked construction for years, (eg. Si/GaAs, Si/InP, and Si/InGaAs. Proposed is use of Si/Strained InGaAs to enable detecting 2.2 micron in the J.A. Woollam IR-VASE (Registered Trademark) Ellipsometer System which operates in the electromagnetic wavelength range of 2-33 microns. Also proposed is use of Three (3) layer Stacked Detector Elements.

The J.A. Woollam IR-VASE System provides Dual Detector capability, variable Angle-of-Incidence capability and utilizes an Alignment mechanism in which a Laser beam is entered thereinto by way of an externally mounted Laser Source and Mirror combination. Once Alignment is accomplished using the highly collimated Laser beam, the Mirror is reoriented to allow entry of polychromatic IR wavelength range electromagnetic radiation. In that light it is disclosed that it is known to provide a source of electromagnetic radiation and cause it to reflect perpendicularly from a surface of a sample so that the orientation of the source of the electromagnetic beam is known, then to rotate/tilt the sample to set it such that said electromagnetic beam approaches it along an oblique angle, and then to move the sample in a direction perpendicular to its surface so that a reflected electromagnetic beam enters a present data detector. Said technique is utilized in the J.A. Woollam CO. VUV-VASE System, for instance. It is also known to focus a beam of electromagnetic radiation which approaches a surface of a sample onto a very small spot and reflects therefrom, and without tending to any sample rotation/tilting move the sample along a substantial perpendicular to said sample surface until a reflected beam optimally enters a present detector. Where a focused beam is utilized the spot size is sufficiently small that a slight tilt of the sample has little effect on the trajectory of the reflected beam. This technique is utilized in systems produced by Nanometrics Inc.

As alluded to, where UV wavelength range electromagnetic radiation is utilized, the atmosphere can not be allowed to contain Oxygen or $H_2O$ vapor. As materials such as electrical wire coatings generally absorb such components, the J.A. Woollam CO. VUV-VASE is presently being re-designed to place substantially all electrical wiring, and other such materials, outside the substantially enclosed chamber. This enables relatively quick purging with such as Nitrogen or Argon and reduces contamination that otherwise might accumulate on sensitive optical surfaces and/or samples under study.

Another feature of the J.A. Woollam CO. VUV-VASE is that the electromagnetic beam is chopped by a lock-in frequency and phase sensitive amplifier which is synchronized with detection. This enables a modulation signal, typically at 266 Hz, which is demodulated by detector related circuitry. It is noted that the J.A. Woollam CO. VUV-VASE utilizes a Rotating Analyzer which is rotated during data acquisition at 14.88 Hz, a much lower rate than is the chopping frequency and that the modulation produces sidebands at (266+/−14.88) HZ of which one is usually utilized. It is also noted that typically data is acquired over a 300 Analyzer rotation period, and an averaged value is provide.

The J.A. Woollam CO. VUV-VASE utilizes a Touch Screen Control approach, although key or mouse aided or any functional means for entry of control instructions can be utilized.

Both the J.A. Woollam CO. VUV-VASE and IR-VASE Systems typically include an Auto-Retarder System which enables said Rotating Analyzer based Systems to obtain data in ranges in which conventional Rotating Polarizer and Rotating Analyzer Ellipsometer Systems alike have been unable to provide reliable accurate and/or precise data. The Auto-Retarder is sequentially positioned after a Stepwise Rotatable Polarizer and enables sequentially modifying a polarization state set by said polarization state setting means, through a plurality of polarization states. Said Auto-Retarder is described in patent to Green No. U.S. Pat. No. 5,956,145, and comprises a selected from the group consisting of:

a. at least one Variable Retarder(s) positioned such that said at least one Variable Retarder(s) and Sample System per se. form a Composite Sample System as seen by said ellipsometer system, and such that a Sample System analyzing polarized light beam is caused to interact with said at least one Variable Retarder(s) and Sample System per se. during use, thereby experiencing a polarization state change; which said at least one Variable Retarder(s) is selected from the group consisting of:

a. a system of at least two waveplate-type Retarders selected from the group consisting of zero-order-waveplate-type Retarders and multi-order-waveplate-type Retarders, which waveplate-type retarders can be rotated with respect to one another, each about an axis perpendicular to an Optical axes thereof, said Optical axes being essentially parallel to the surface of said waveplate-type Retarders;

b. a Babinet dual wedge-type Variable Retarder;

c. a Soleil dual wedge-type Variable Retarder;

d. a Kerr electro-optical-type Variable Retarder;

e. a Pockels electro-optical-type Variable Retarder;

f. a Liquid Crystal electro-optical-type Variable Retarder;

g. a Voigt magnetic-Faraday-effect Variable Retarder;

h. a Cotton-Mouton magnetic-Faraday-effect Variable Retarder;

i. a Berek-type Variable Retarder, the optical axis of which is oriented essentially perpendicular to the surface thereof, which Berek-type Retarder can be tilted about multiple axes to align said optical axis such that it is coincident with an incident polarized beam of light and thereby cause only a negligible attenuation effect, rather than a polarization state changing effect thereon; and such that in use adjusting of a present said at least one Variable Retarder(s) places at least the DELTA of said Composite Sample System is placed within a range in which the PSI and DELTA of said Composite Sample System can be usably accurately and precisely investigated by said ellipsometer system.

Relevant Co-Owned Patents are:

U.S. Pat. No. 5,757,494 to Green et al.;

U.S. Pat. No. 5,956,145 to Green et al.;

which teach system and method for improving data acquisition capability in spectroscopic ellipsometers;

U.S. Pat. No. 5,872,630 to Johs et al.;

which describes a rotating compensator ellipsometer system and documents conception of the idea of using a quad detector in automated beam alignment;

U.S. Pat. No. 6,034,777 to Johs et al.;

which describes a method of correcting for the effect of windows in a vacuum chamber, hence the application of ellipsometer systems in controlled environment chambers;

U.S. Pat. No. 5,661,589 to Meyer;

which describes a bilateral slit control system which is applied in monochromators; and and in Co-Owned and Co-Pending Allowed patent application Ser. No. 09/531,877;

Additional patents disclosed for general background are: U.S. Pat. No. 5,582,646 to Woollam et al.; U.S. Pat. No. 5,963,327 to He et al.; U.S. Pat. No. 6,456,376 to Liphardt et al.; U.S. Pat. No. 5,582,646 to Woollam et al.; U.S. Pat. No. 4,210,410 to Batten; U.S. Pat. No. 5,045,704 to Coates; U.S. Pat. No. 5,045,701 to Goldstein et al.; U.S. Pat. No. 4,472,633 to Motooka; U.S. Pat. No. 5,486,701 to Norton et al.; U.S. Pat. No. 5,706,212 to Thompson et al.; and Application US2002/0024668 A1 of Stehle et al.

Even in view of the prior art, need remains for improvements on, additions to and new combinations of described ellipsometer and the like systems and methods. Said improvements being, for instance, in the areas of systems and methods involving monochromators, sample alignment, the setting of angles of incidence of a beam to a sample, use of environment control chambers and signal detectors.

DISCLOSURE OF THE INVENTION

The disclosed invention is a sample sequestering means in an ellipsometer or polarimeter system which is suitable for analyzing samples using electromagnetic radiation wavelengths which are adversely affected by typical atmospheric components. Said ellipsometer or polarimeter system comprises, within a structural framework, a chamber means for encompassing a substantially enclosed space. Said chamber means has functionally incorporated thereinto, a subspace of said substantially enclosed space. In said subspace is a sample securing stage which provides means for causing a sample to be oriented to face substantially upward during sample loading, and for placing and maintaining a sample in a desired position and orientation facing other than substantially upward during application of electromagnetic radiation thereto and data acquisition. Said chamber further comprises means for entering a flow of purging gas from said substantially enclosed space generally into said subspace. Said sample sequestering means is distinguished in that it provides means for allowing open atmosphere access to said sample securing stage in said subspace without said subspace being sequestered from said substantially enclosed space generally.

During use, a flow of purging gas from said substantially enclosed space generally into said subspace is at a constant volumetric rate unless the subspace is open to atmosphere by operation of the sample sequestering means to allow access to the Sample Securing Stage. When the subspace is open to atmosphere a means for causing increase of the flow of purging gas from said substantially enclosed space generally into said subspace operates to increase the flow of said purging gas. This increased flow serves to discourage atmospheric components, such as oxygen and water vapor from entering the subspace. The means for allowing open atmosphere access to said sample securing stage in said subspace without said subspace being sequestered from said substantially enclosed space generally, comprises a cover means which can be positioned in closed and open positions. Said cover can be hinge mounted to said structural framework, and said lid can comprise a transparent portion which enables looking into said subspace while said lid is closed.

The ellipsometer or polarimeter system comprises the following components, in said substantially enclosed space, in any functional order:

a) source means for providing of a beam of electromagnetic radiation including wavelengths which are adversely affected by atmospheric components (eg. in the ultraviolet range);

b) polarization state setting means for setting a polarization state in at least a selected small range of wavelengths in a beam including ultraviolet wavelength range electromagnetic radiation;

c) means which enables sequentially modifying a polarization state set by said polarization state setting means, through a plurality of polarization states;

d) alignment detector means comprising a plurality of detector elements surrounding a substantially centrally located hole through which a beam of electromagnetic radiation can pass, said substantially centrally located hole preferably having a diameter sufficiently large such that about ten times more intensity of a beam passes therethrough than does through a hole of 1.27 mm;

e) data detector means for receiving an electromagnetic beam which is caused to interact with a sample which is secured in place by said means for placing and maintaining a sample in a desired position and orientation;

f) monochromator means, for selecting a small range of wavelengths in a beam of electromagnetic radiation, present between said source means for providing of a beam of electromagnetic radiation and said data detector means for receiving an electromagnetic beam which is caused to interact with a sample;

and in said subspace, between said means which enables sequentially modifying a polarization state set and said data detector means:

g) said sample securing stage providing means for causing a sample to be oriented to face substantially upward during sample loading, and for placing and maintaining a sample in a desired position and orientation other than facing substantially upward during application of electromagnetic radiation thereto and data acquisition.

The ellipsometer system further comprises, typically outside the substantially enclosed space:

h) computer means for analyzing data provided by said data detector means for receiving an electromagnetic beam after it interacts with said sample.

It is noted that the source means, polarization state setting means, and means which enables sequentially modifying a polarization state set by said polarization state setting means are typically sequentially in the order recited above, with the sample securing stage providing means positioned thereafter and preceeding the data detector means. The monochromator, however, can be in any functional location.

The disclosed invention can also be described as ellipsometer or polarimeter system comprising:

in a substantially enclosed space:

a) source means for providing of a beam of electromagnetic radiation including wavelengths which are adversely affected by atmospheric components (eg. ultraviolet range electromagnetic radiation);

b) polarization state setting means for setting a polarization state in at least a selected small range of wavelengths;

c) means which enables sequentially modifying a polarization state set by said polarization state setting means, through a plurality of polarization states;

d) alignment detector means comprising a plurality of detector elements surrounding a substantially centrally located hole through which a beam of electromagnetic radiation can pass, said substantially centrally located hole preferably having a diameter sufficiently large such that about ten times more intensity of a beam passes therethrough than does through a hole of 1.27 mm;

e) data detector means for receiving an electromagnetic beam which is caused to interact with a sample which is secured in place by said means for placing and maintaining a sample in a desired position and orientation;

and in a subspace of said substantially closed space present between said means which enables sequentially modifying a polarization state set and said data detector means:

f) a sample securing stage providing means for causing a sample to be oriented to face substantially upward during sample loading, and for placing and maintaining a sample in a desired position and orientation other than facing substantially upward during application of electromagnetic radiation thereto and data acquisition;

said ellipsometer system further comprising:

h) computer means for analyzing data provided by said data detector means for receiving an electromagnetic beam after it interacts with said sample.

The disclosed invention further includes a spectrophotometer system comprising:

in a substantially enclosed space:

a) source means for providing of a beam of electromagnetic radiation including wavelengths which are adversely affected by atmospheric components, (eg. ultraviolet range electromagnetic radiation);

c) alignment detector means comprising a plurality of detector elements surrounding a substantially centrally located hole through which a beam of electromagnetic radiation can pass, said substantially centrally located hole preferably having a diameter sufficiently large such that about ten times more intensity of a beam passes therethrough than does through a hole of 1.27 mm;

d) data detector means for receiving an electromagnetic beam which is caused to interact with a sample which is secured in place by said means for placing and maintaining a sample in a desired position and orientation;

and in a subspace of said substantially closed space present between said source means and said data detector means:

e) a sample securing stage providing means for causing a sample to be oriented to face substantially upward during sample loading, and for placing and maintaining a sample in a desired position and orientation other than facing substantially upward during application of electromagnetic radiation thereto and data acquisition;

said spectrophotometer system further comprising:

h) computer means for analyzing data provided by said data detector means for receiving an electromagnetic beam after it interacts with said sample.

A method of investigating a sample with a spectrophotometer, ellipsometer or polarimeter system utilizing wavelengths which are adversely affected by atmospheric components, comprises the steps of:

A) providing a spectrophotometer, ellipsometer or polarimeter system aw described above;

B) operating said subspace means for allowing open atmosphere access thereto;

C) causing said sample securing stage providing means to face substantially upward and loading a sample thereonto;

D) causing said sample securing stage providing means to place and maintain a sample in a desired position and orientation other than facing substantially upward E) causing electromagnetic radiation from said source means for providing of a beam including wavelengths which are adversely affected by atmospheric components to interact with said sample, and enter said data detector;

F) entering data from said data detector into said computer means for analyzing data;

said method being distinguished by causing purging gas from said means for causing purging gas to flow into said substantially enclosed space generally and therefrom into said subspace at a substantially constant volumetric rate during data acquisition, but at an increase volumetric flow rate when the subspace of said substantially enclosed space is operated to allow open atmosphere access thereto while a sample is loaded to said sample securing stage, when it is caused to face substantially upward.

The present invention can also be described as a sample sequestering means in a spectrophotometer, ellipsometer or polarimeter system which is suitable for analyzing samples using electromagnetic radiation with wavelengths which are adversely affected by typical atmospheric components, said spectrophotometer, ellipsometer or polarimeter system comprising, within a structural framework, a chamber means for encompassing a substantially enclosed space;

said chamber means having functionally incorporated thereinto a subspace of said substantially enclosed space, in which subspace is a sample securing stage, said sample securing stage providing means for causing a sample to be oriented to face in a loading position during sample loading, and for placing and maintaining a sample in a desired position and orientation facing other than in said loading position during application of electromagnetic radiation thereto and data acquisition;

said chamber further having means for entering a flow of purging gas from said substantially enclosed space generally into said subspace;

said sample sequestering means being distinguished in that it provides means for allowing open atmosphere access to said sample securing stage in said subspace without said subspace being sequestered from said substantially enclosed space generally.

For general insight, and to provide contrast, the following provides excerpts from Pending Utility application Ser. No. 10/376,677, which Application is incorporated herein by reference.

Previous Vacuum Ultraviolet (VUV) Ellipsometer System

As a specific example of a disclosed invention ellipsometer system for analyzing sample systems using electromagnetic radiation with wavelengths in the ultraviolet wavelength range, said ellipsometer system can be described as comprising a chamber means which encompasses a substantially enclosed space, functionally within said substantially enclosed space there being present:

a) source means for providing of a beam including ultraviolet wavelength range electromagnetic radiation;

b) polarization state setting means for setting a polarization state in at least a selected small range of wavelengths in a beam including ultraviolet wavelength range electromagnetic radiation;

c) means which enables sequentially modifying a polarization state set by said polarization state setting means, through a plurality of polarization states;

d) alignment detector means comprising a plurality of detector elements surrounding a substantially centrally located hole through which a beam of electromagnetic radiation can pass, said substantially centrally located hole having a diameter sufficiently large such that about ten times more intensity of a beam passes therethrough than does through a hole of 1.27 mm;

e) a means for placing and maintaining a sample system in a desired position and orientation, (optionally a vacuum chuck), said means for placing and maintaining a sample system in a desired position and orientation being positioned in a subspace of said substantially enclosed space which can be sequestered by a subspace sequestering means;

f) data detector means for receiving an electromagnetic beam which is caused to interact with a sample system which is secured in place by said means for placing and maintaining a sample system in a desired position and orientation; and g) computer means for analyzing data provided by said data detector means for receiving an electromagnetic beam after it interacts with said sample system;

h) monochromator means, for selecting a small range of wavelengths in a beam including ultraviolet wavelength range electromagnetic radiation, present between said source means for providing of a beam including ultraviolet wavelength range electromagnetic radiation and said data detector means for receiving an electromagnetic beam which is caused to interact with a sample system.

Said chamber means has functionally affixed thereto means for causing said subspace sequestering means to become configured so as to sequester a sample system in a subspace of said substantially enclosed space, or to open and expose said sample system generally to the substantially enclosed space, and means for accessing said means for placing and maintaining a sample system in a desired position and orientation.

Said chamber further has means having functionally affixed thereto means for entering purging gas into said substantially enclosed space generally, and to a subspace sequestered by said subspace sequestering means independently when it is caused to be sequestered from said substantially enclosed space.

In use a sample system is caused to be affixed to said means for placing and maintaining a sample system in a desired position and orientation via said means for accessing said means for placing and maintaining a sample system in a desired position and orientation, and purging gas is caused to be entered into said substantially enclosed space via said means for entering purging gas into said substantially enclosed space generally, and/or to a subspace sequestered by said subspace sequestering means independently when it is caused to be sequestered from said substantially enclosed space, and said source means for providing of a beam including ultraviolet wavelength range electromagnetic radiation is caused to provide a beam including ultraviolet wavelength, and said polarization state setting means for setting a polarization state in a selected small range of wavelengths in a beam including ultraviolet wavelength range electromagnetic radiation is caused to impose a polarization state thereupon and said beam of ultraviolet wavelength range electromagnetic radiation is caused to pass through said hole in said alignment detector means comprising a plurality of detector elements surrounding a substantially centrally located hole, and said monochromator means for selecting a small range of wavelengths in said beam of ultraviolet wavelength range electromagnetic radiation is caused to provide a small range of wavelengths in said beam of ultraviolet wavelength range;

such that said means for placing and maintaining a sample system in a desired position and orientation is caused to orient said sample system so that said beam including ultraviolet wavelength range electromagnetic radiation is caused to reflect essentially directly back from said sample system such that the signals from each of the alignment detector means of said plurality of detector elements provide optimum signal output, and then, without removing said alignment detector means of said plurality of detector elements, causing said means for placing and maintaining a sample system in a desired position and orientation is caused to reorient said sample system such that said beam including ultraviolet wavelength range electromagnetic radiation impinges thereupon at a known angle of incidence;

and such that said beam including ultraviolet wavelength range electromagnetic radiation interacts with said sample system and then enters said data detector.

The disclosed invention will be better understood by reference to the Detailed Description Section of this Specification in conjunction with the Drawings.

SUMMARY OF THE INVENTION

It is therefore a purpose and/or objective of the present invention to provide a sample sequestering system which allows access to a subspace in a chamber encompassed generally enclosed space, for use in entering and removing a sample when the subspace is opened to atmosphere.

It is another purpose and/or objective of the present invention to teach flow of sufficient purge gas from within the generally enclosed space into the subspace to discourage atmospheric contaminates from entering into the subspace and adversely a spectrophotometer, ellipsometer or polarimeter or the like system which operates at wavelengths, (eg. UV), which are adversely affected, (eg. absorbed), by typical atmospheric contents, located in the generally enclosed space.

Other purposes and/or objectives of the present invention will be apparent from a reading of the Specification and Claims.

BRIEF DESCRIPTION OF THE DRAWINGS

FIGS. 5a and 5b are side views of Lid (L) in closed and open orientations respectively.

DETAILED DESCRIPTION

Figure 1:
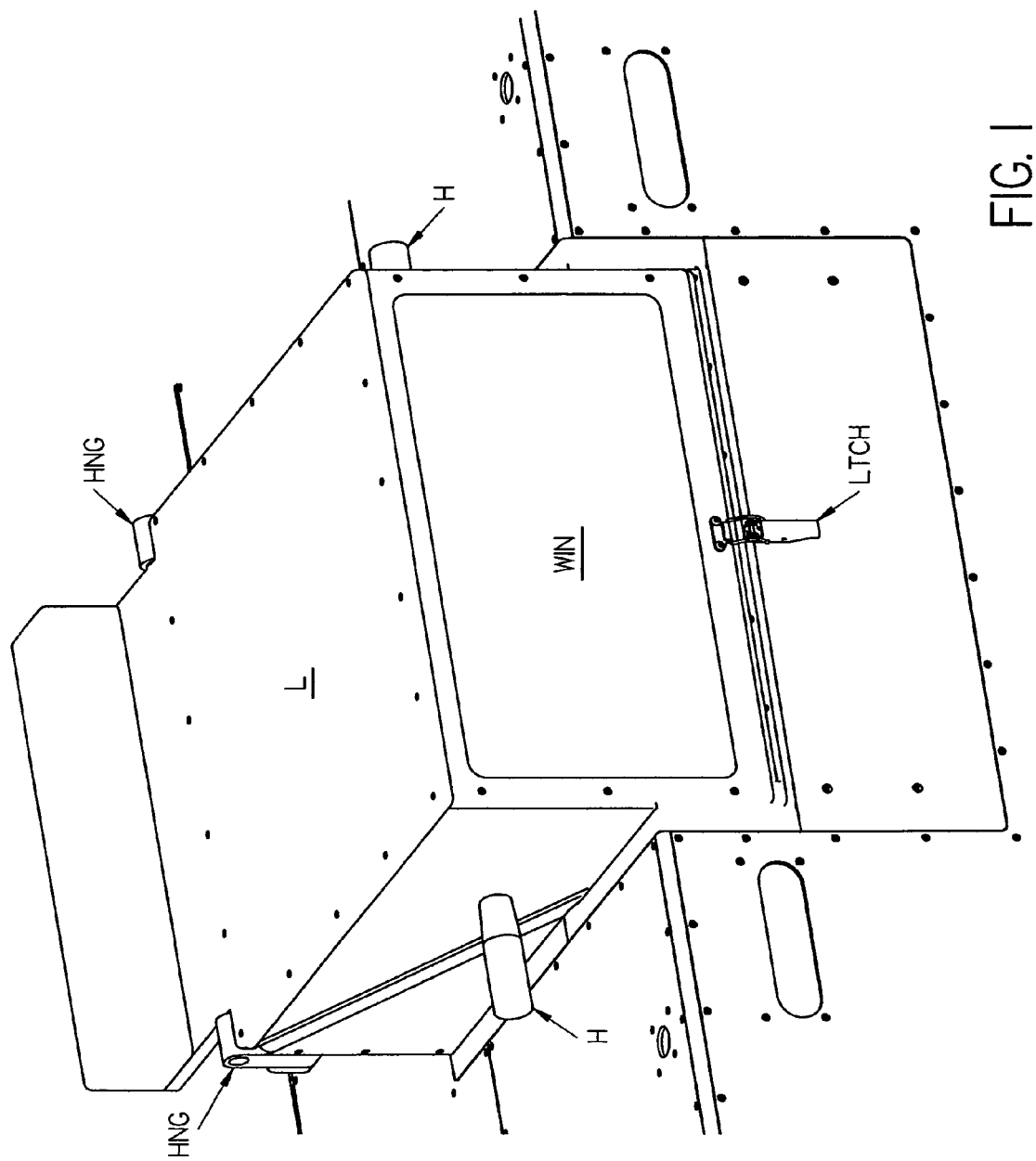
FIG. 1 shows a Newly Designed and Realized J.A. Woollam CO. Inc. Sample Entry System in a Vacuum Ultraviolet (VUV) Ellipsometer System, in perspective, looking from the left and from slightly thereabove.
Figure 2:
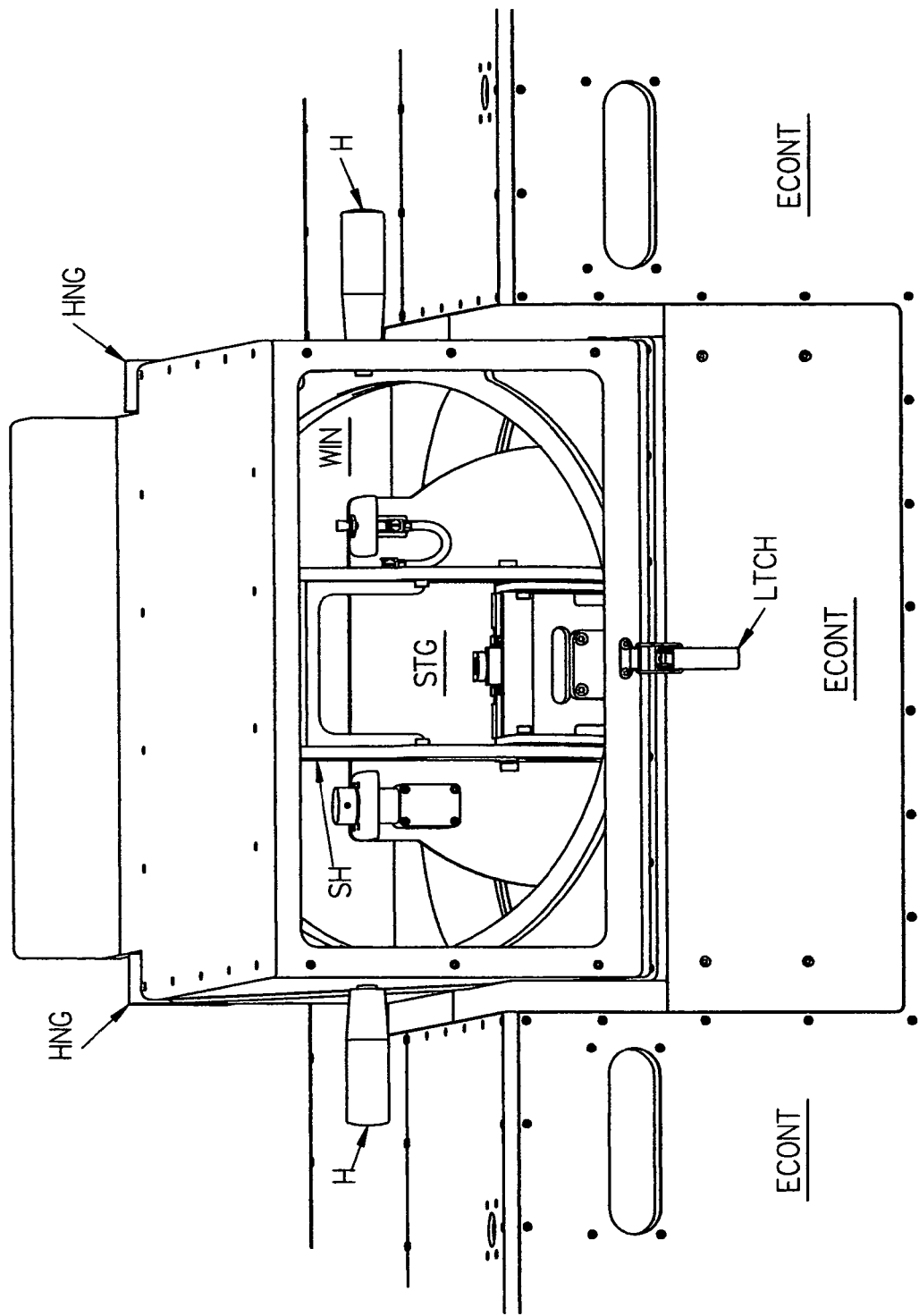
FIG. 2 shows the same system as in FIG. 1, looking from in front thereof.
Figure 3:
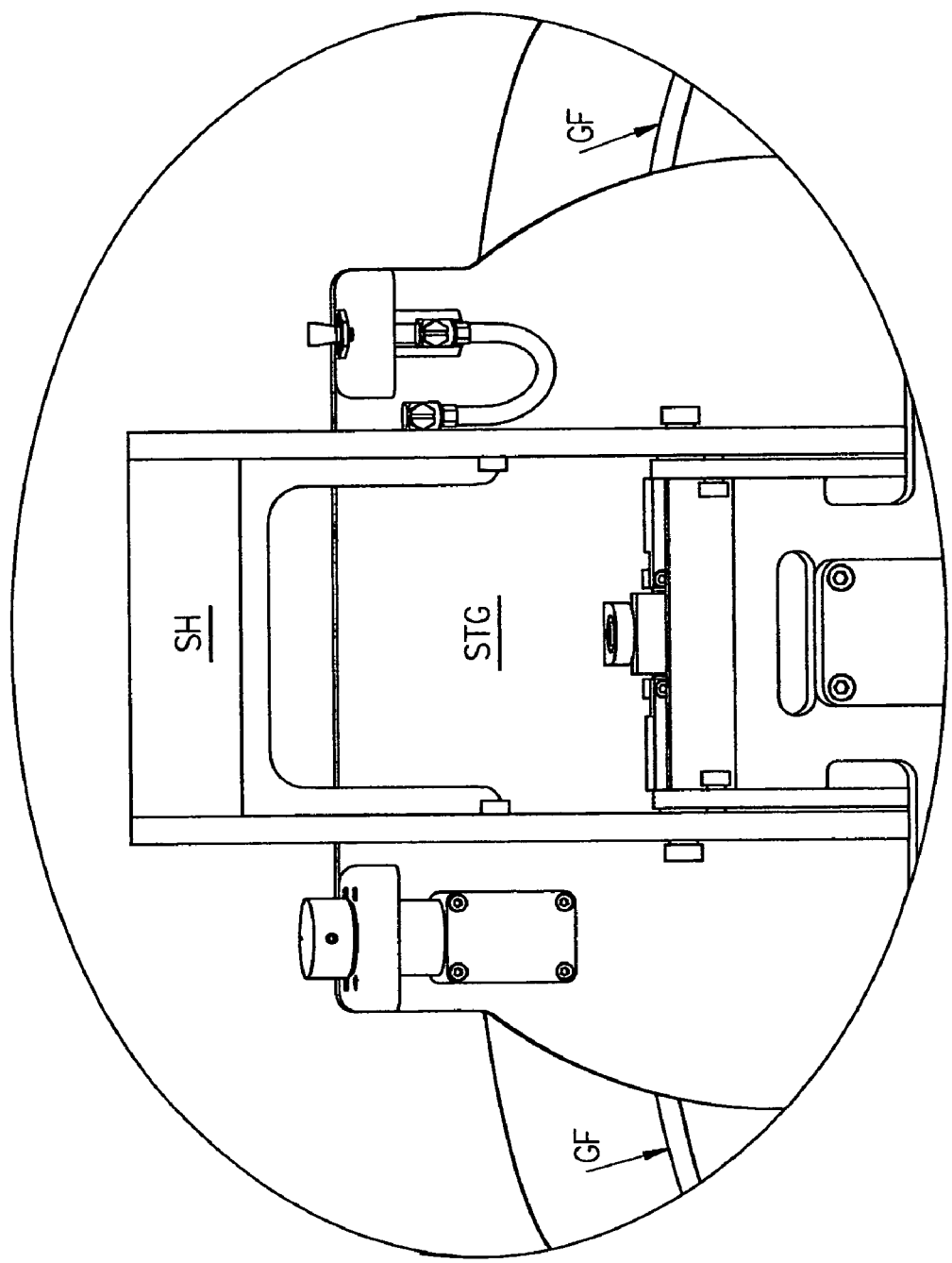
FIG. 3 shows the systems of FIGS. 1 and 2 after the handles (H) have been used to push front of the Lid (L) upward causing rotation about Hinge (HNG).
Figure 4:
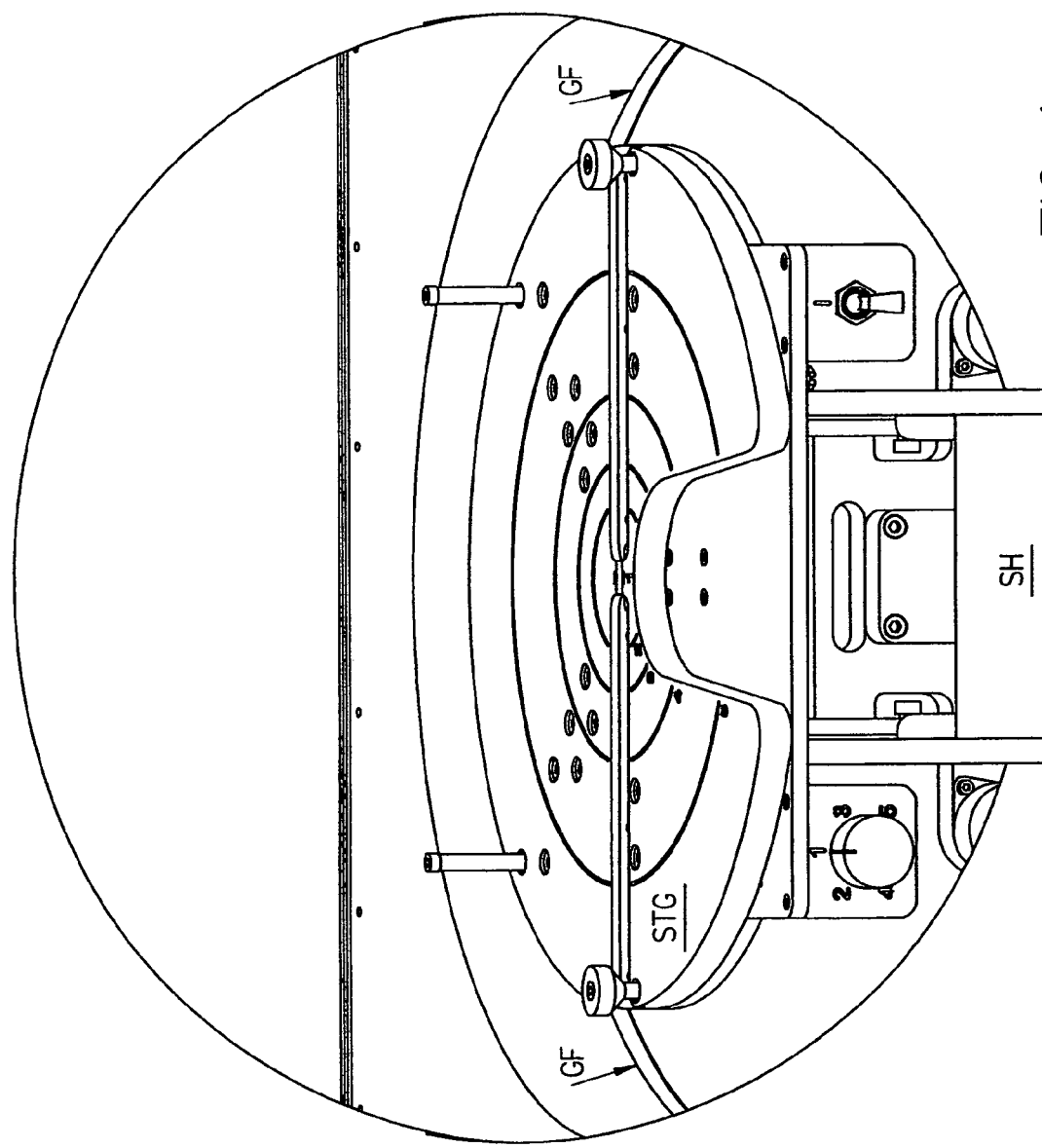
FIG. 4 shows the Sample Securing Stage (STG) which becomes available in a horizontally orientation when the Sample Securing Means Stage Handle (SH) is caused to be rotated downward.

FIG. 1 shows a Newly Designed and Realized J.A. Woollam CO. Inc. Sample Entry System in a Vacuum Ultraviolet (VUV) Ellipsometer System, in perspective, looking from the left and from slightly thereabove. Note the Handles (H), and a hinge (HNG) at the back of the Lid (L). FIG. 2 shows the same system as in FIG. 1, looking from in front thereof. Note the Latch (LTCH) which serves to keep the Lid (L) secured in use, (said lid (L) keeps atmospheric contaminates out of the subspace it sequesters when it is positioned as shown in FIGS. 1 and 2. Also note FIG. 2 indicates the Container of an Ellipsometer (ECONT) System which is a Chamber means that encompasses a substantially Enclosed Space therewithin. As configured in FIGS. 1 and 2, it should be appreciated that open atmosphere is prevented from entering a sequestered subspace which contains the elements shown in FIGS. 3 and 4. FIG. 3 shows the systems of FIGS. 1 and 2 after the handles (H) have been used to push front of the Lid (L) upward causing rotation about Hinge (HNG) and thereby allowing access to the Sample Securing Means Stage Handle (SH), (see indication of where the Stage Handle (SH) is located in FIG. 2 when the Lid (L) is closed). FIG. 4 shows the Sample Securing Stage (STG) which becomes available in a horizontally orientation when the Sample Securing Means Stage Handle (SH) is caused to be rotated downward. Note that FIG. 3 also shows Gas Flow (GF) slit openings through which gas is flowed in use to prevent contamination from entering into the substantially enclosed space within the Ellipsometer Container (ECONT) shown in FIG. 2. When said Lid (L) is closed, (see FIGS. 1 and 2), gas is caused to flow from the Gas Flow (GF) slit openings at a maintenance rate. When the Lid (L) is lifted up, however, as shown in FIGS. 3 and 4 to allow access to the Sample Securing Stage (STG), gas is caused to flow at an increased rate from Gas Flow (GF) Slit to discourage open atmosphere components from entering into the subspace defined by the Lid (L) when it is closed. It is noted that a Cole-Parmer Volumetric Flowmeter Catalog Number A-32907-00 through A32907-72 or A32908-64 through A32908065 can be utilized to cause a flow of gas through the Gas Flow (GF) slit opening in use. It is also specifically noted that while not limiting, the Sample Securing Stage (STG) can include vacuum chuck capability which allows easily securing and releasing a sample by providing a suction, or not. In addition, the Stage (STG) for securing a Sample System can also contain a heating and/or cooling means for controlling the temperature of a sample.

Figure 6B:
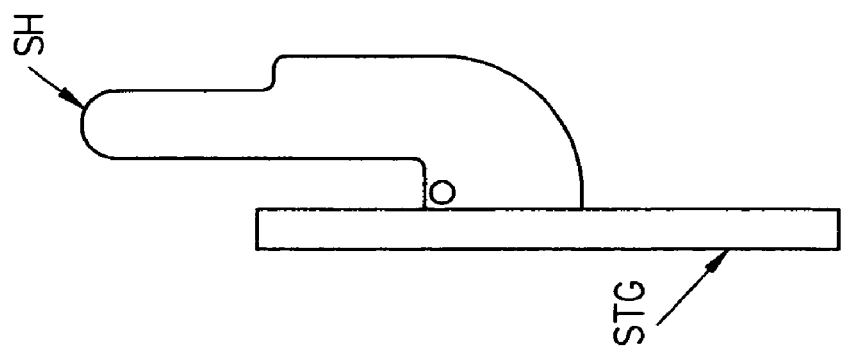
FIGS. 6a and 6b show side views of the Sample Securing Stage (STG) in Sample loading and Sample analysis orientations respectively.
Figure 6A:
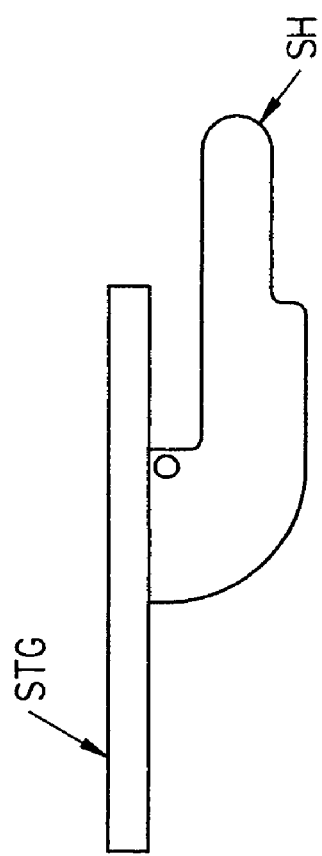

FIGS. 5a and 5b are side views of Lid (L) in closed and open orientations respectively, and FIGS. 6a and 6b show side views of the Sample Securing Stage (STG) in Sample loading and Sample analysis orientations respectively.

Figure 7A:
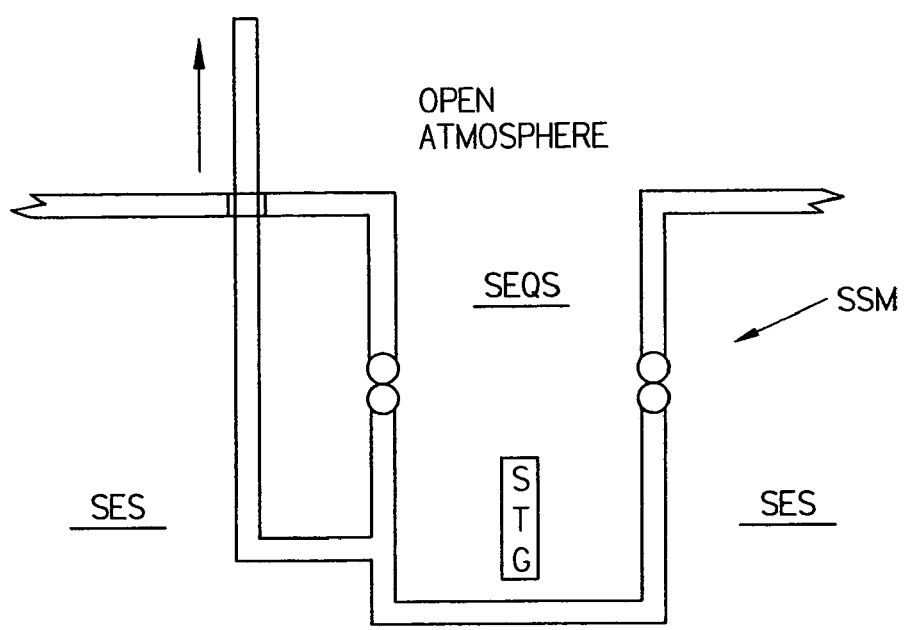
FIGS. 7a, 7b and 8 from Co-Pending Utility application Ser. No. 10/376,677, for comparison to the presently disclosed invention.
Figure 7B:
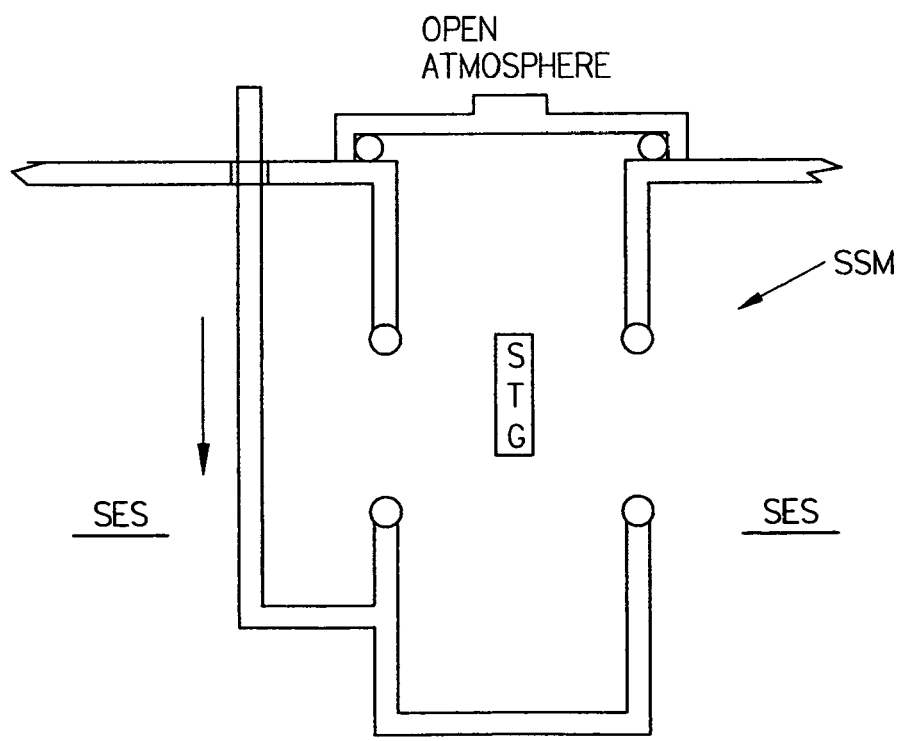
Figure 8:
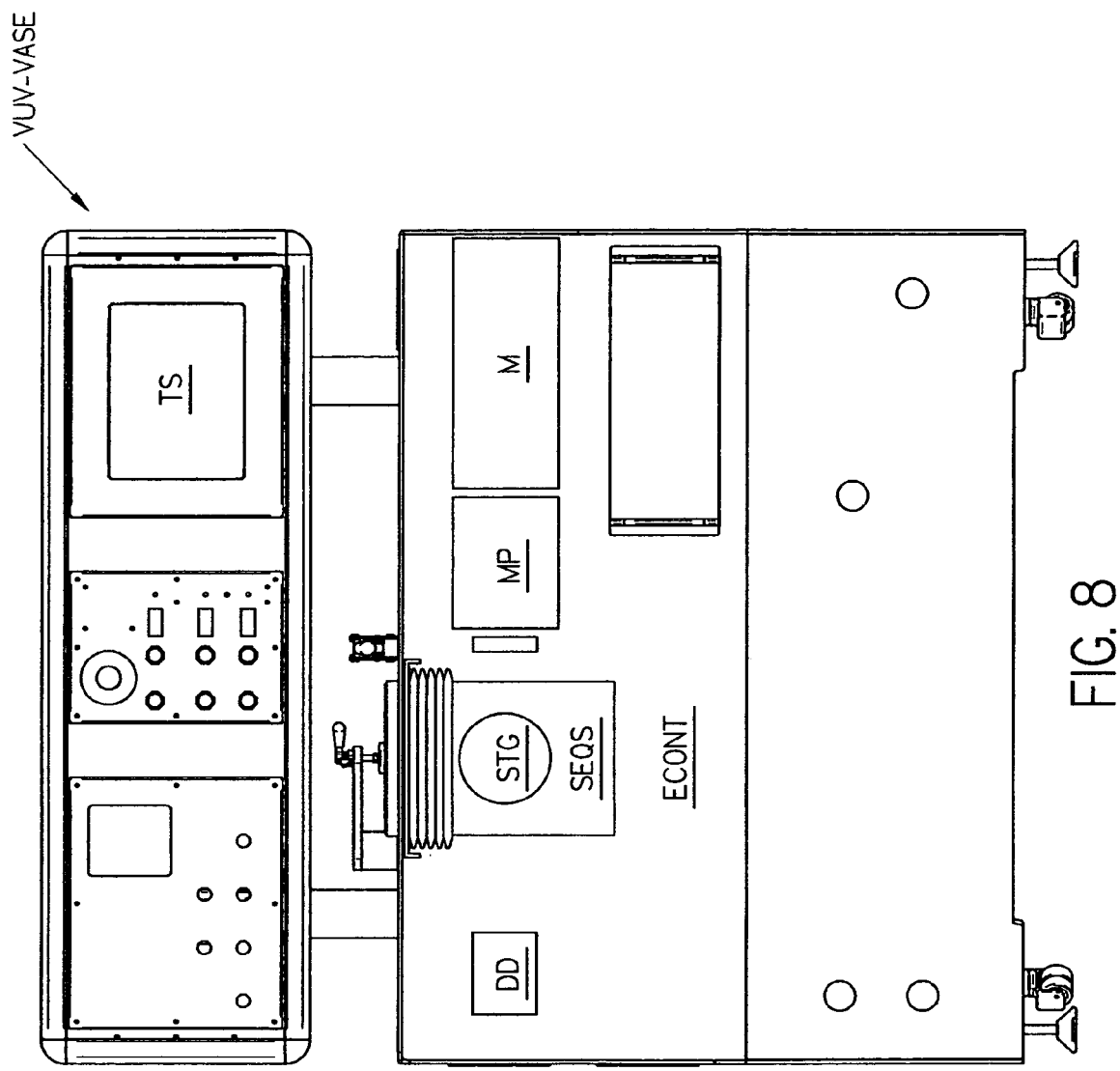

For comparison and differentiation, included herewith are FIGS. 7a, 7b and 8 from Co-Pending Utility application Ser. No. 10/376,677, which Drawings show a chamber means which has functionally affixed thereto means for causing said subspace sequestering means to become configured so as to sequester a sample system in a subspace of said substantially enclosed space, or to open and expose said sample system generally to the substantially enclosed space, and means for accessing said means for placing and maintaining a sample system in a desired position and orientation. FIG. 7a shows a means for placing and maintaining a sample system in a desired position and orientation (STG), said means for placing and maintaining a sample system in a desired position and orientation being positioned in a sequestered subspace (SEQS) of said substantially enclosed space (SES) which can be sequestered by a subspace sequestering means (SSM). FIG. 7b shows the subspace sequestering means (SSM) of FIG. 7a opening the means for placing and maintaining a sample system in a desired position and orientation on Sample Securing Stage (STG) to the substantially enclosed space (SES).

Figure 9:
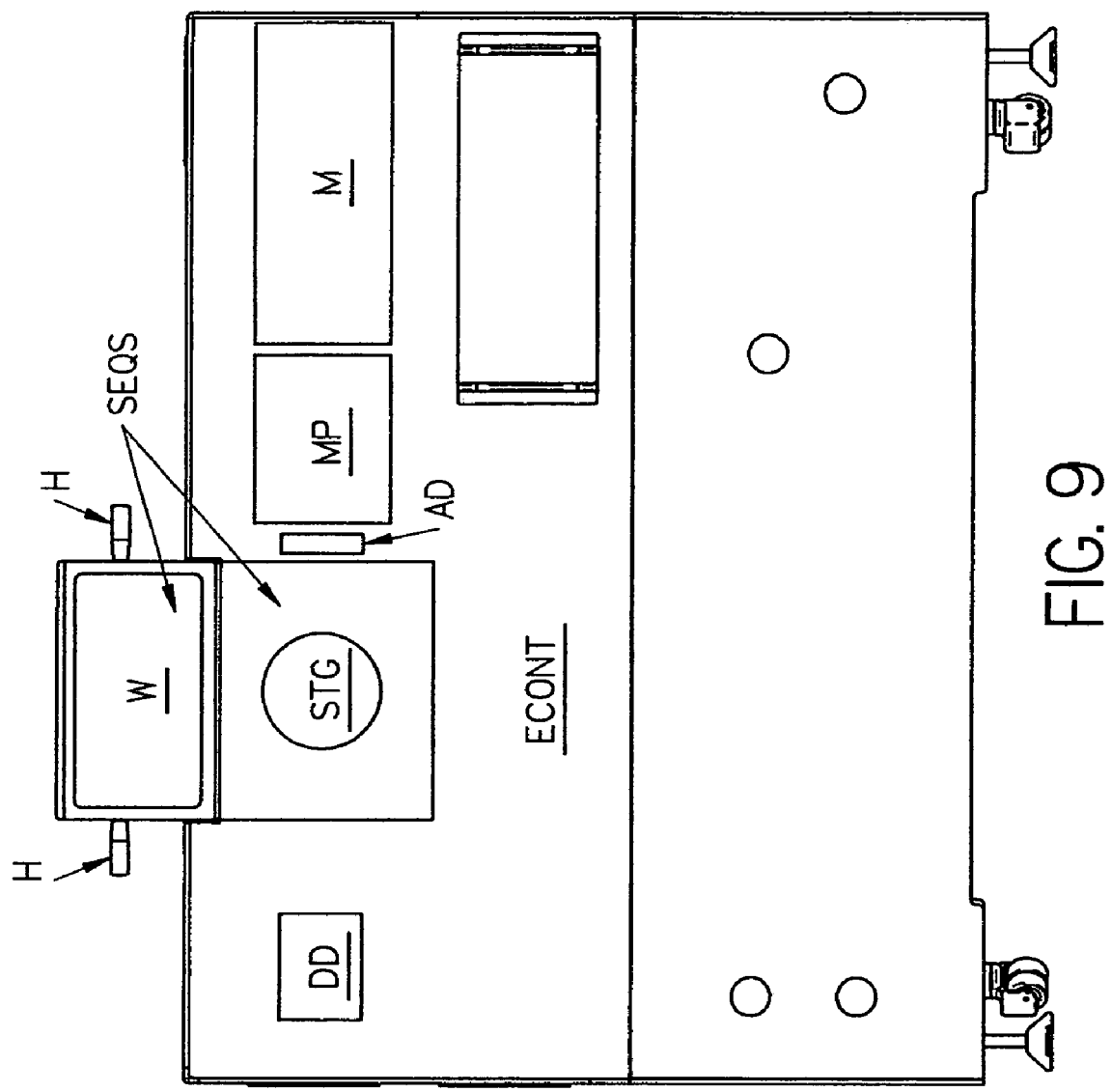
FIG. 9 provides a front elevational view showing the general layout of the J.A. Woollam Co. VUV-VASE as Claimed herein.

FIG. 8 provides a front elevational view showing the general layout of the J.A. Woollam Co. VUV-VASE which incorporates the design demonstrated in FIGS. 7a and 7b. FIG. 9 provides a front elevational view showing the general layout of the J.A. Woollam Co. VUV-VASE as Claimed herein. Note the presence of the Monochromator (M), means which enables sequentially modifying a polarization state set by said polarization state setting means, through a plurality of polarization states (MP), Alignment Detector, means for placing and maintaining a sample system in a desired position and orientation, (Sample Securing Stage (STG)), said means for placing and maintaining a sample system in a desired position and orientation being positioned in a sequestered subspace (SEQS) of said substantially enclosed space (SES) which can be sequestered by a subspace sequestering means (SSM), and multiple detector system (MDET). Also indicated is a Touch Screen (TS) Control. As FIGS. 7a and 7b show the previous approach to maintaining the enclosed space (SES) free from contamination when loading and unloading a sample from the Sample Securing Stage (STG) therein (note it is indicated as oriented vertically rather than horizontally as is Sample Securing Stage (STG) in FIG. 4), involved forming a sequestered space (SEQS) and opening it to atmosphere during said sample loading an unloading, and closing access to atmosphere and opening the sequestered space to the (SES) during data acquisition. The improvement exemplified in FIGS. 1-4 makes said sequestered space (SEQS) formation unnecessary. Because gas is caused to flow out of Gas Flow (GF) Slit when the Lid (L) is raised upward via rotation about Hinge (HNG) by applying upward force to Handles (H), to provide access to the Stage (STG) shown in FIG. 4, contamination can not enter into the chamber (ECONT) through said Gas Flow (GF) Slit. It is noted that during data acquisition an electromagnetic beam is directed to a Sample on said Stage (STG) through said Gas Flow (GF) Slit.

Figure 10:
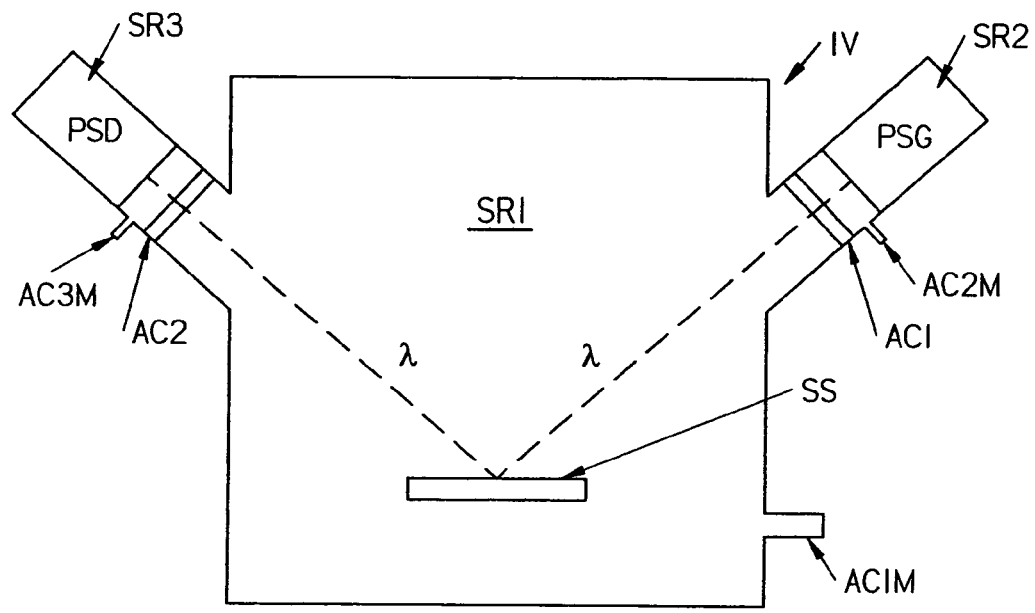
FIG. 10 demonstrates that an environmental control chamber can comprises multiple regions which can be separately sequestered.
Figure 12:
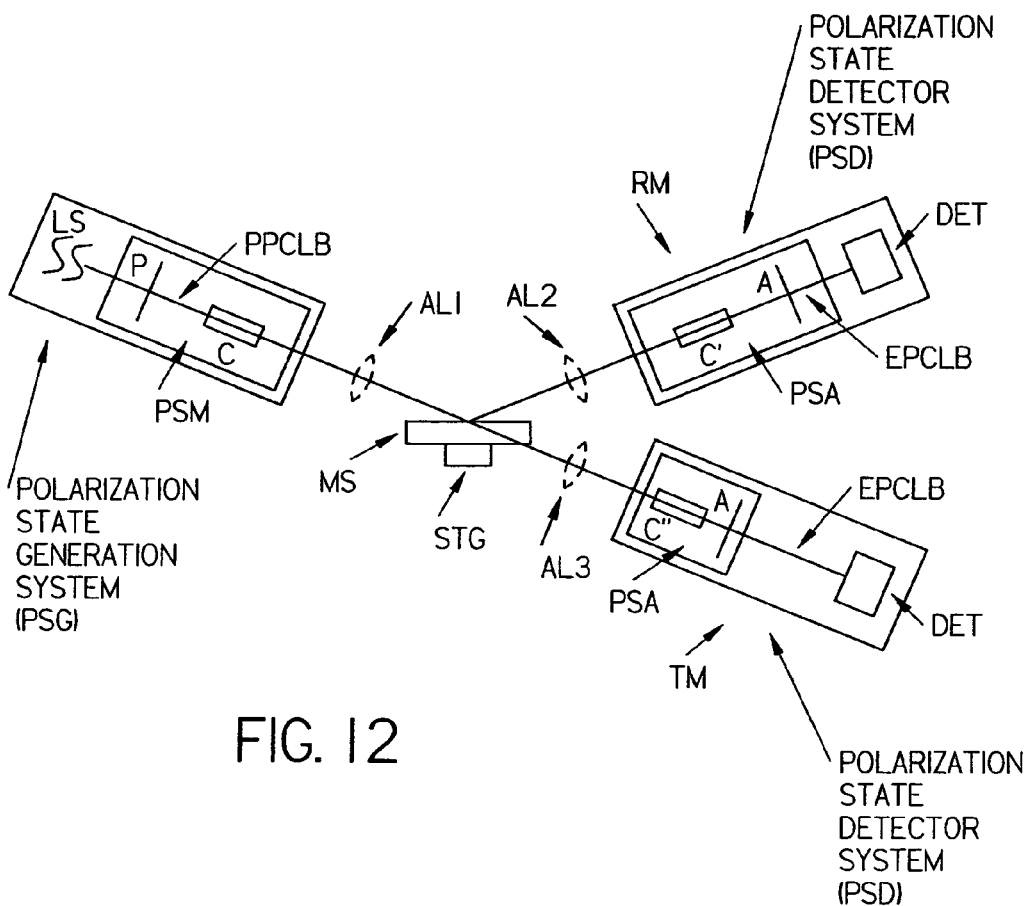
FIG. 12 provides insight to ellipsometer and polarimeter systems.

For general insight FIG. 10 demonstrates that an environmental control chamber can comprises multiple regions which can be separately sequestered. Said FIG. 10 can be considered to be, functionally, a top view of the systems shown in FIGS. 8 and 9. Shown are separate regions in which are present a Sample (SS), a Polarization State Generator (PSG) and a Polarization State Detector (PSD). Note that Ambient Control Means (AC1M), (AC2M) and (AC3M) are associated with said sequestered regions ((SR1), (SR2) and (SR3) respectively and allow entry of purging gas or evacuation of their associated sequestered region. Sequestering Means (AC1) and (AC2), (eg. windows), separate the Sequestered Regions (SR2) from (SR1) and (SR1) from (SR3) respectively. The environment in each sequestered region can then be separately controlled. Note that sequestered region (SR1) can represent either (SES) or (SEQS) in FIG. 10. FIG. 12 is included to give better insight to ellipsometer and polarimeter systems. Better shown are that a Polarization State Generator (PSG) can comprise a Source of Electromagnetic Radiation (LS), a Polarizer (P) and optionally a Compensator (C); and that a Polarization State Detector (PSD) can comprise a Detector (DET), Analyzer (A) and optionally a Compensator (C') (C''). Note, both Reflection and Transmission configurations are shown.

Figure 11:
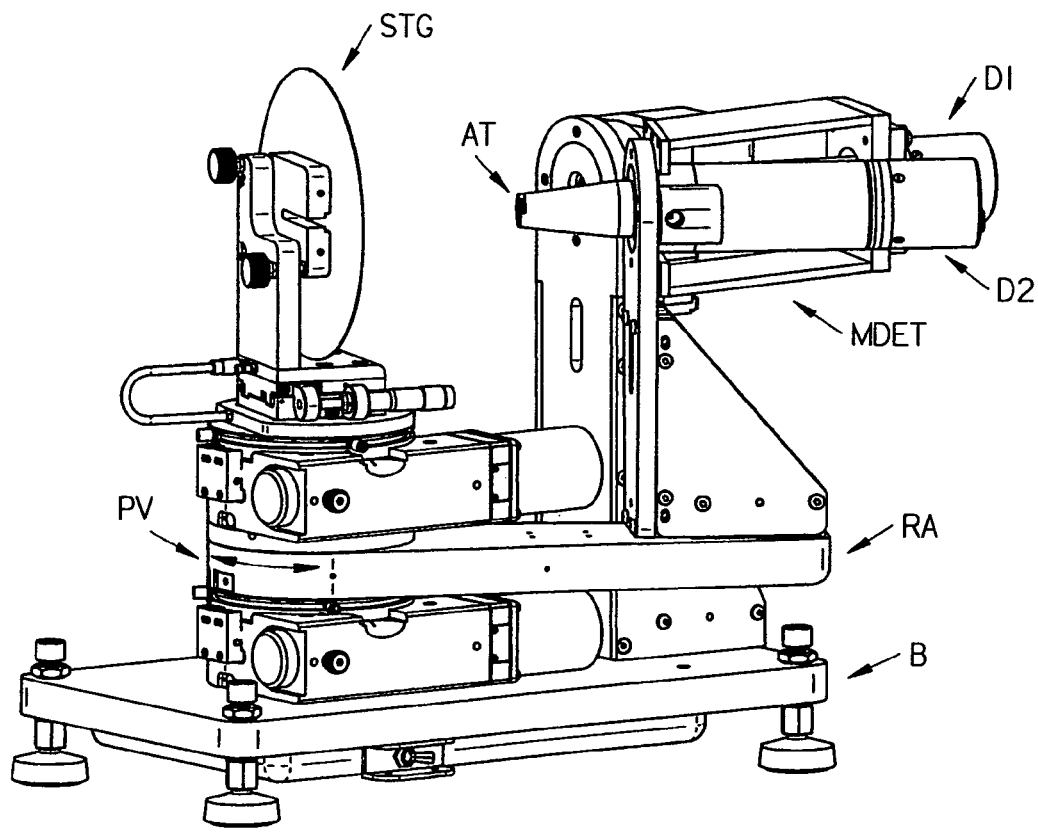
FIG. 11 demonstrates that a Detector (DD) can be comprised of multiple detectors (D1) (D2).

FIG. 11 demonstrates that a Detector (DD) can be comprised of multiple detectors (D1) (D2), (as a group (MDET)), which are pivotally mounted (PV) to allow easily moving them into the path of an electromagnetic beam which reflects from a sample on the Sample Securing Stage (STG). Also shown are a Base (B), Rotating Arm (RA), and an optional Aperture (AP) which can be used to limit the diameter of a beam allowed to enter a detector. This can be of benefit when Sample alignment is being performed.

Figure 13:
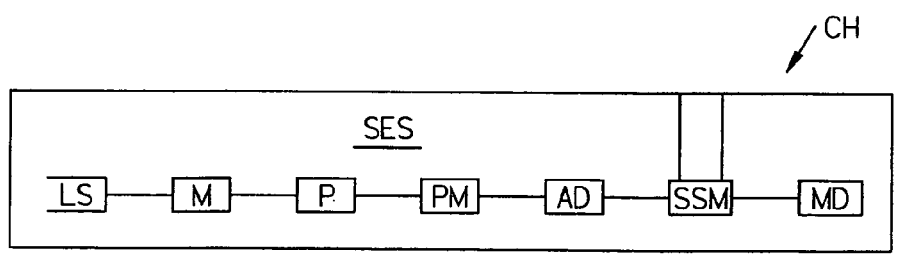
FIG. 13 is included to demonstrate a preferred sequence of components in a disclosed ellipsometer and polarimeter system.

FIG. 13 is included to demonstrate a preferred sequence of components in the disclosed ellipsometer and polarimeter system. Within a Chamber (CH)are shown are a Source of Electromagentic Radiation (LS), a Monochromater (M), a Polarizer (P), a means for modifying polarization state (PM) (eg. a Compensator (C), an Alignment Detector (AD), a Subspace Sequestering Means (SSM) and a Data Detector (MD).

FIGS. 1-6b and 9 then demonstrate a new Sample Entry System applied to a J.A. Woollam Co. Inc. VUV-VASE (Registered Trademark), System. Said new Sample Entry System allows easy entry and mounting of Samples on a Sample Securing Stage (STG), while it is conveniently oriented to face substantially upward. Access to the Sample Securing Stage (STG) is direct via an opened Lid (L), (see FIG. 5a), while purge gas is caused to flow at a sufficient volumetric rate to discourage atmospheric components from entering into the subspace defined by the closed Lid (D), (see FIG. 5b).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A sample sequestering means in an ellipsometer or polarimeter system which is suitable for analyzing samples using electromagnetic radiation with wavelengths which are adversely affected by typical atmospheric components, said ellipsometer or polarimeter system comprising, within a structural framework, a chamber means for encompassing a substantially enclosed space;

said ellipsometer or polarimeter system in said substantially enclosed space comprising:
  a) source means for providing of a beam of electromagnetic radiation including wavelengths which are adversely affected by atmospheric components;
  b) polarization state setting means for setting a polarization state in at least a selected small range of wavelengths in a beam including;
  c) means which enables sequentially modifying a polarization state set by said polarization state setting means, through a plurality of polarization states;
  d) data detector means for receiving an electromagnetic beam which is caused to interact with a sample which is secured in place by said means for placing and maintaining a sample in a desired position and orientation;

e) monochromator means, for selecting a small range of wavelengths in a beam of electromagnetic radiation including wavelengths which are adversely affected by atmospheric components, present between said source means for providing of a beam of electromagnetic radiation and said data detector means for receiving an electromagnetic beam which is caused to interact with a sample;

said chamber means having functionally incorporated thereinto a subspace of said substantially enclosed space, in which subspace is a sample securing stage, said sample securing stage providing means for causing a sample to be oriented to face substantially upward during sample loading, and for placing and maintaining a sample in a desired position and orientation facing other than substantially upward during application of electromagnetic radiation thereto and data acquisition;

said chamber further having means for entering a flow of purging gas from said substantially enclosed space generally into said subspace;

said sample sequestering means being distinguished in that it provides means for allowing open atmosphere access to said sample securing stage in said subspace without said subspace being sequestered from said substantially enclosed space generally.

2. A sample sequestering means as in claim 1 in which comprises means for causing a flow of purging gas from said substantially enclosed space generally into said subspace at a substantially constant volumetric rate.

3. A sample sequestering means as in claim 1 which comprises means for causing increase rate of flow of purging gas from said substantially enclosed space generally into said subspace, when the subspace of said substantially enclosed space is open to atmosphere by operation of the sample sequestering means to allow access to the Sample Securing Stage.

4. A sample sequestering means as in claim 1 in which said means for allowing open atmosphere access to said sample securing stage in said subspace without said subspace being sequestered from said substantially enclosed space generally, comprises a cover means which can be positioned in closed and open positions.

5. A sample sequestering means as in claim 4 in which said cover means is lid which is hinge mounted to said structural framework, within which is said chamber means for encompassing a substantially enclosed space.

6. A sample sequestering means as in claim 5 in which said lid comprises a transparent portion which enables looking into said subspace while said lid is closed.

7. A sample sequestering means as in claim 1 which further comprises an alignment detector means comprising a plurality of detector elements surrounding a substantially centrally located hole through which a beam of electromagnetic radiation can pass, said substantially centrally located hole having a diameter sufficiently large such that about ten times more intensity of a beam passes therethrough than does through a hole of 1.27 mm.

8. A sample sequestering means as in claim 1 which further comprises computer means for analyzing data provided by said data detector means for receiving an electromagnetic beam after it interacts with said sample.

9. A sample sequestering means in a spectrophotometer, ellipsometer or polarimeter system which is suitable for analyzing samples using electromagnetic radiation with wavelengths which are adversely affected by typical atmospheric components, said spectrophotometer, ellipsometer or polarimeter system comprising, within a structural framework, a chamber means for encompassing a substantially enclosed space;

said chamber means having functionally incorporated thereinto a subspace of said substantially enclosed space, in which subspace is a sample securing stage, said sample securing stage providing means for causing a sample to be oriented to face in a loading position during sample loading, and for placing and maintaining a sample in a desired position and orientation facing other than in said loading position during application of electromagnetic radiation thereto and data acquisition;

said chamber further having means for entering a flow of purging gas from said substantially enclosed space generally into said subspace;

said sample sequestering means being distinguished in that it provides means for allowing open atmosphere access to said sample securing stage in said subspace without said subspace being sequestered from said substantially enclosed space generally, in that said means for entering a flow of purging gas from said substantially enclosed space generally into said subspace comprises means for causing purging gas from said means for causing purging gas to flow into said substantially enclosed space generally and therefrom into said subspace at a substantially constant volumetric rate during data acquisition, but at an increase volumetric flow rate when the subspace of said substantially enclosed space is operated to allow open atmosphere access thereto while a sample is loaded to said sample securing stage, when said stage is caused to face substantially upward.

* * * * *